(12) United States Patent
Fernandez et al.

(10) Patent No.: US 7,309,439 B2
(45) Date of Patent: Dec. 18, 2007

(54) MAGNETIC BEAD MANIPULATION AND TRANSPORT DEVICE

(75) Inventors: Victor Fernandez, Dundee (GB); Amar Rida, Prilly (CH); Martin Gijs, Ecublens (CH)

(73) Assignee: Ecole Polytechnique Federale de Lausanne (EPFL), Lausanne (CH)

(*) Notice: Subject to any disclaimer, the term of this patent is extended or adjusted under 35 U.S.C. 154(b) by 127 days.

(21) Appl. No.: 11/214,571

(22) Filed: Aug. 30, 2005

(65) Prior Publication Data
US 2005/0284817 A1 Dec. 29, 2005

Related U.S. Application Data

(63) Continuation of application No. PCT/IB03/00956, filed on Mar. 8, 2003.

(51) Int. Cl.
*B01D 35/06* (2006.01)
*G01N 33/553* (2006.01)

(52) U.S. Cl. ............ 210/695; 210/660; 210/222; 210/223; 210/502.1; 436/526

(58) Field of Classification Search ............ 210/660, 210/695, 222, 223, 502.2, 502.1; 417/50; 436/526
See application file for complete search history.

(56) References Cited

U.S. PATENT DOCUMENTS

| | | | |
|---|---|---|---|
| 4,916,081 A | 4/1990 | Kamada | |
| 5,541,072 A | 7/1996 | Wang | |
| 5,779,892 A | 7/1998 | Miltenyi | |
| 6,013,188 A | 1/2000 | Terstappen | |
| 6,132,607 A | 10/2000 | Chen | |
| 6,193,892 B1 | 2/2001 | Krueger | |
| 2003/0012693 A1 | 1/2003 | Otillar et al. | |

FOREIGN PATENT DOCUMENTS

WO  WO 99/49319  9/1999
WO  WO 02/31505  4/2002

OTHER PUBLICATIONS

Copy—pp. 175-178—DNA Quantification with an Electrochemiluminesce Microcell—Techn. Digest Transducers '97—Hsueh et al.
Copy—pp. 151-158—A Fully Integrated Micromachined Magnetic Particle Separator—Journal of Microelectromechanical etc. Sep. 1996.

(Continued)

*Primary Examiner*—David A. Reifsnyder
(74) *Attorney, Agent, or Firm*—Sturm & Fix LLP

(57) ABSTRACT

A device for transporting magnetic or magnetizable microbeads (25) in a capillary chamber (14) comprises a permanent magnet (10) or an electromagnet (11) for subjecting the capillary chamber to a substantially uniform magnetic field, to apply a permanent magnetic moment to the microbeads (25). At least one planar coil (22) and preferably an array of overlapping coils are located adjacent to the capillary chamber (14) for applying a complementary magnetic field on the microbeads parallel or antiparallel to said substantially uniform magnetic field, to drive the microbeads. An arrangement is provided for switching the current applied to the coil(s) (22) to invert the field produced thereby, to selectively apply an attractive or repulsive driving force on the microbeads (25). The device is usable to transport microbeads for performing chemical and biochemical reactions or assay, as is done for instance in clinical chemistry assays for medical diagnostic purposes.

24 Claims, 5 Drawing Sheets

OTHER PUBLICATIONS

Copy—pp. 409-416—An on-chip magnetic bead separator using spiral electromagnets with semi-encapsulated permalloy—BIOSENSORS 2001.

Copy—pp. 156-162—A novel approach to the automation of clinical chemisty by controlled manipulation of, etc.—Journal of . . . (1999).

Copy—pp. 1775-1777—Manipulation of magnetic microbeads in suspension using micromagnetic . . . —Applied Physics Letters 2001.

Copy—pp. 3308-3310—Microelectromagnets for the control of magnetic nanoparticles—Applied Physics Letters—Nov. 12, 2001.

Copy—pp. 262-276—Magnetic design considerations for devices and particles used for . . . Journal of Magnetism and Magnetic (2001).

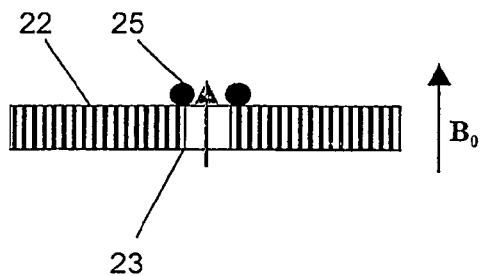
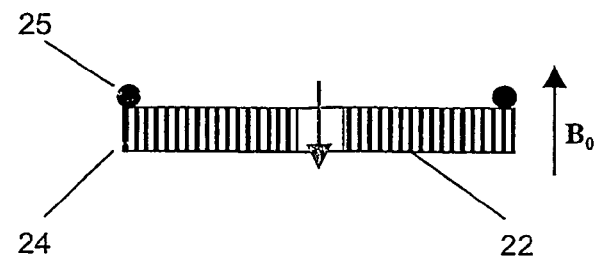
Fig. 6  Fig. 7
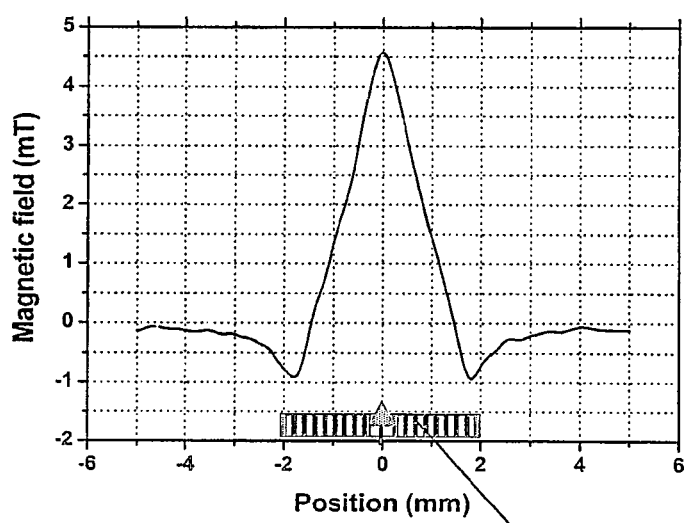
Fig. 5

MAGNETIC BEAD MANIPULATION AND TRANSPORT DEVICE

CROSS REFERENCE TO RELATED APPLICATIONS

This application is a Continuation application of PCT/IB03/000956 filed Mar. 8, 2003, which is included in its entirety by reference made hereto.

FIELD OF THE INVENTION

This invention relates to devices for manipulation and transport of magnetic beads. The invention concerns in particular an apparatus of the above-mentioned kinds wherein the magnetic beads are used for performing chemical and biochemical reactions or assays, as is done for instance in clinical chemistry for medical diagnostic purposes.

BACKGROUND OF THE INVENTION

It is known that magnetic particles ('beads') embedded in a liquid can be used to carry a probe molecule on their surface that specifically interacts with a complementary target molecule (for example single stranded probe DNA interacting with complementary target DNA). Upon reaction with a molecule to be probed and, for example, using optical or electrochemical measurements, one can determine the amount of target molecules on a bead or within a certain volume containing beads (see for example Hsueh et al., Techn. Digest Transducers '97, p. 175 (1997)). The interest in using magnetic microbeads, is that they can be manipulated using magnetic fields irrespective of fluid motion. In this way one can create an important relative motion of the beads with respect to the fluid and, hence, a large probability of binding a target molecule to a probe molecule fixed on the bead surface. One can then magnetically extract the beads to a place of detection/collection. Historically, beads have been locally fixed by using external magnets or have been transported using mechanically moving external magnets. The latter procedure may be for example used to fabricate mixing devices (Sugarman et al., U.S. Pat. No. 5,222,808) and in immuno-assay methods (Kamada et al., U.S. Pat. No. 4,916,081).

"Separation" of magnetic microbeads means that a liquid flow, containing the beads, passes a zone with a large magnetic field (gradient) and that the magnetic microbeads are filtered out (separated) by the field. U.S. Pat. No. 5,779,892 describes the use of a permanent magnet to separate (filter) the magnetic microbeads from a passing liquid solution. U.S. Pat. No. 6,013,188 describes a ferromagnetic capture structure, made of a Ni grid and placed in the field of a permanent magnet to select magnetic microbeads from a liquid solution that passes through the grid. Other patents on separation of magnetic beads are U.S. Pat. No. 6,132,607 and the US patents mentioned therein. Finally, U.S. Pat. No. 6,193,892 describes how a rack that is to hold containers with magnetically responsive solutions is configured with permanent magnets to extract the magnetic microbeads from the solution. U.S. Pat. No. 5,541,072 concerns the creation of magnetic clusters (ferrophases) that are transported by a permanent magnet. Ahn et al. [C. H. Ahn, M. G. Allen, W. Trimmer, Y. J. Yun, and S. Erramilli, J. Microelectromechanical Syst. 5, 151-158, 1996] have reported magnetic bead separation device using integrated inductive components; in follow-up work, electroplated spiral coils in Cu were combined with an electroplated permalloy yoke structure to separate microbeads from a liquid solution passing over an array of coils [J.-W. Choi, T. M. Liakopoulos, and C. H. Ahn, Biosens. & Bioelectronics 16, 409-416, 2001]. The coils were arranged spaced apart from one another side-by-side. As the magnetic field is localised over an area of the order of the coil width, the described simple juxtaposition of the coils will not enable microbead transport, but merely allow separation of the microbeads. With this proposal, the microbeads were retained and separated by action of a magnetic field generated by the coil, but it was not possible to transport the beads by the action of the magnetic field. Transporting the beads required using a liquid flow.

Magnetic transport of beads is essential for bringing the beads to a well-defined position within a microfluidic circuit, for example near to a magnetic bead detection device. "Transport" means that the microbeads are effectively moved by a magnetic force, i.e. using a magnetic field and not just retained by a magnetic field from a liquid solution passing by (=separation). Nevertheless, manipulation of these beads in general and transport in particular, is a difficult task, as the effective relative magnetic susceptibility $\chi_{\it eff}$ of the (super)paramagnetic beads is rather weak (typically $\chi_{\it eff} \ll 1$, due to demagnetization effects of the mostly spherical particles) and the magnetic volume of the particles is small. This explains why mostly the large field of (mechanically moving) permanent magnets or large electromagnets have been used for the separation, transport, and positioning of magnetic microbeads [See webpage of Miltenyi Biotec Inc., Auburn, Calif.: http://www.miltenyibiotec.com.; S. Østergaard, G. Blankenstein, H. Dirac, and O. Leistiko, J. Magn. Magn. Mat. 194, 156-162, 1999 and WO 99/49319]. In other work, micropatterned conductors, actuated by large currents, have been demonstrated to present a useful solution for magnetic microbeads capture and transport. These devices allow precise positioning and transport over 10-100 µm distances in a single actuation event [T. Deng, G. M. Whitesides, M. Radhakrishnan, G. Zabow, and M. Prentiss, Appl. Phys. Lett. 78, 1775-1777, 2001; C. S. Lee, H. Lee, and R. M. Westervelt, Appl. Phys. Lett. 79, 3308-3310, 2001].

In the work of Deng et al., the field of a permanent magnet placed at some distance beneath the device has been combined with the field generated by the current through an electrical conductor. Here, the electrical conductor was made of two side-by-side serpentine wires shifted linearly in phase by $\pi/3$, that generated a magnetic field having local field maxima in every turn and with opposite directions in neighbouring turns. However, the generated magnetic field gradient (several 0.1 T/mm) is localized over a small distance (~100 µm) which leads to the consequence that many actuation steps are necessary to transport beads through a large surface area rapidly. This disadvantage is particularly serious for application in biotechnology, where it is desirable to rapidly transport beads over distances of several millimetres which requires several hundreds of actuation steps with this serpentine wire arrangement. Also the magnetic field generated by a single wire is weak, so that large currents (of the order of $10^6$ A/mm$^2$) are required to transport the microbeads over these small distances.

WO 02/31505 describes the use of an electromagnetic chip to transport and detect the presence of magnetic beads.

In previous work on magnetic bead transport, the moving magnetic field is obtained by mechanically moving a permanent magnet (magnetic induction of the order of 0.1-1.5 Tesla), which is a very large value that can induce an important magnetic moment in the microbead (the magnetic moment is given by $\mu=V\chi_{eff}B_0$, with $B_0$ the magnetic field generated by the permanent magnet, $\chi_{eff}$ the magnetic permeability and V the magnetic microbead volume). One should realize that a very small microbead has no effective magnetization when there is no external field, ie it is superparamagnetic. The magnetic force on such moment in a total magnetic induction field B is given by:

$$F = \frac{\mu}{\mu_0} \nabla B \quad (1)$$

making it clear that a strong magnetic force is obtained when having a large moment AND a large gradient of the magnetic induction. To have appreciable magnetic forces, relatively important magnetic fields (about $10^{-2}$ T) and large magnetic field gradients (from 10 to 100 T/m) must be generated locally [G. P. Hatch, and R. E. Stelter, "Magnetic design considerations for devices and particles used for biological high-gradient magnetic separation (HGMS)", J. Magnetism Magn. Materials 225, pp. 262-276, 2001]. A permanent magnet hence delivers a large force, but the problem is that it is cumbersome in generating a 'moving' field.

On the other hand, the magnetic field generated by a coil fed with a current can be varied in time easily but is very small. Typically fields of just a few milliTesla are generated by a simple coil using currents of the order of 0.1-1 Amp. When looking at equation (1), it is clear that the magnetic moment of the microbead will be typically a factor 1000 smaller and that also the magnetic gradient will be a factor 10 smaller. The consequence is that magnetic forces of coils can be easily varied in space and time but that the forces are too small to effectively transport the microbeads. An improvement would be to fabricate a magnetic yoke structure made of a soft magnetic material around the coil, which amplifies somewhat the magnetic field that is generated by the coil (typically a factor 10).

However, the prior art does not disclose any effective way of using simple coils to displace magnetic beads.

SUMMARY OF THE INVENTION

An object of the invention is to provide a device for manipulating and/or transporting microbeads employing simple planar coils which generate low magnetic fields to displace microbeads through longer distances at higher speeds than were heretofore possible.

A further object of the invention is provide such a device employing simple technology, notably Printed Circuit Board (PCB) technology for the manufacture of the coils, together with simple permanent magnets or electromagnets.

The invention proposes a novel approach for magnetic microbead transport in a capillary chamber over long-range distances using at least one coil, and, preferably, using an array of simple planar coils. The coil(s) is/are placed in a uniform static magnetic field, the role of which is to impose a permanent magnetic moment to the microbeads. The very small magnetic field gradient of a simple planar coil is then sufficient to displace the microbeads.

The invention thus provides a simple planar coil array-based magnetic microbead transport system, in which an individual coil is capable of displacing beads over millimeter distances in a liquid-containing capillary. A drastic increase of the magnetic energy and magnetic forces acting on the beads is obtained by placing the coil array in a uniform static magnetic field that imposes a permanent magnetic moment to the microbeads. The very small magnetic field (gradient) of a simple planar coil is then sufficient to displace the microbeads over a distance of the order of the coil size. Arranging adjacent coils with spatial overlap and actuating them in a specific phase (for example a three-phase scheme) assures the long-range displacement of the microbeads A preferred embodiment of the invention concerns a two-dimensional array of coils that can be operated collectively to induce microbead transport, which can be used for the manipulation and/or transport of microbeads.

The inventive microbead transport system is based on the use of a coil, preferably a set of planar coils obtainable by simple Printed Circuit Board technology, that is/are placed inside the large static magnetic field. This is done in such a way that the magnetic induction is uniform, i.e. it contributes to the formation of the magnetic moment $\mu$, but not to the formation of a gradient $\nabla B$. Thanks to the formation of large magnetic moments (typically a factor 10-100 larger than when using a coil only), the very small field gradients of simple planar coils are sufficient to transport these magnetic microbeads. This becomes especially attractive for very small magnetic particles (nano-beads) that have a very small volume V and are, otherwise, very difficult or impossible to magnetise.

With the inventive device, the magnetic field generated by the coils has a magnetic field gradient localized over a distance equal to the coil width. Consequently, the magnetic field gradient generated by the coils is typically several mT/mm (~10 Gauss/mm), localized in distances measured in a scale of several millimetres. This localisation of the magnetic field gradient is several magnitudes larger than the field gradient localization scale (100 μm) of the above-discussed serpentine wire arrangement. As a further consequence, with the inventive device it is possible to perform a long-range displacement (10-100 mm) in a few actuation steps (2-20, for instance) whereas several hundreds of steps would be necessary to perform the same displacement range using the above-discussed serpentine wire arrangement.

Switching of the coils at a desired frequency can be computer controlled. The maximum switching frequency for any particular device can be determined as a function of the time necessary for a microbead to go from the centre to the border of a coil, which depends in particular on the characteristics of the microbeads and the fluid. For example, where this time is about 0.2 sec, the maximum switching frequency is 5 Hz.

As a result the device according to the invention is applicable in areas requiring rapid microbead displacement, such as compact bio-analysis systems, where magnetic beads are the 'carriers' for the biochemical reactions or play a role in optical, electrical or electrochemical detection of biochemical reactions. This invention can be used in a diagnostic system to detect very low concentration biomolecules. Microbeads can be transported by the magnetic field to a sensor region in the microfluidic circuit or can be used to mix different solutions or enhance the cross section for chemical interaction between the bead and the activated surface (i.e. the chemically activated surface of the plane of the coils). Also, selection and transport of specially marked beads is possible in a two-dimensional coil array structure.

The device can for example comprise a Hall sensor, the coil(s) being arranged to transport the microbeads to the Hall sensor.

Moreover, the widely used and simple PCB technology can be used to integrate the coil system in the device, making manufacture simple and inexpensive. In PCB technology, coils are distributed over at least two functional layers separated by an insulating layer in such a way that electrical short-circuiting between neighbouring coils is avoided.

The invention also relates to a method of transporting microbeads in a fluid in a capillary chamber, which comprises: subjecting the capillary chamber to a substantially uniform magnetic field, to induce a permanent magnetic moment to the microbeads; applying a complementary magnetic field on the microbeads parallel or antiparallel to said substantially uniform magnetic field by means of at least one coil adjacent to the capillary chamber; and switching the current applied to the coils to invert the field produced thereby, to selectively apply an attractive or repulsive driving force on the microbeads. Preferably, the coils are generally planar and the sustantially uniform magnetic field is perpendicular to the planar coils.

Further aspects of the invention are set out in the claims.

BRIEF DESCRIPTION OF THE DRAWINGS

In the accompanying schematic drawings, which are given by way of example:

FIG. 5 is a graph showing the magnetic field generated by a coil;

FIGS. 6 and 7 are sectional views through a coil illustrating the effect of the generated magnetic field respectively to attract or to repel beads;

DETAILED DESCRIPTION

Figure 1:
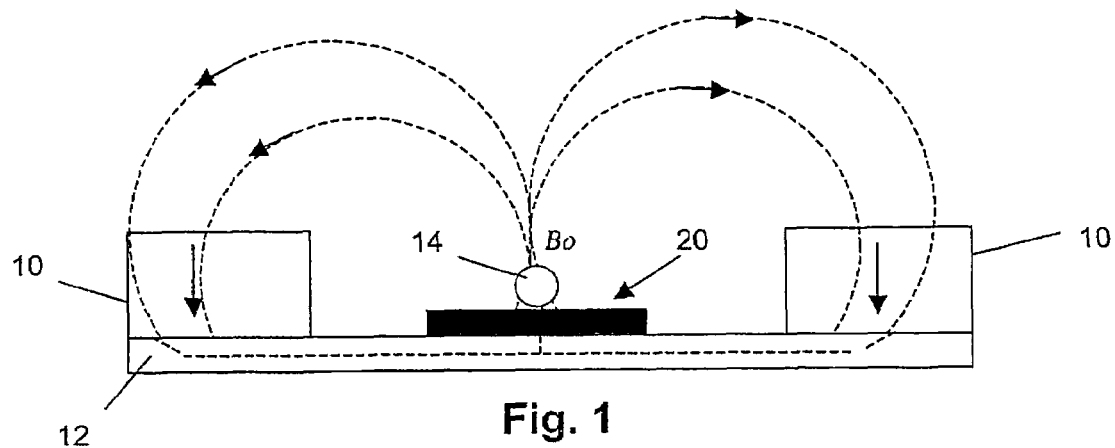
FIG. 1 is a lateral view of a first embodiment of a bead transport device according to the invention, employing two permanent magnets.

A first example of a bead transport structure according to the invention is shown in schematic lateral view in FIG. 1. Two bar-shaped NdFeB permanent magnets 10, for example measuring 40 mm×15 mm×8 mm, are placed on top of a soft magnetic sheet 12, and generate a uniform field $B_0$ (for instance 50 mT) over the total length of a microfluidic glass capillary 14, for instance 1 mm outer diameter, 0.5 mm inner diameter. A coil array 20 is positioned on the magnetic sheet 12 directly underneath the capillary 14.

The capillary 14 contains microbeads in a suitable fluid, for example water. The microbeads typically have dimensions from 0.01 to 10 µm and can be suspended in water and injected in the capillary 14. They can for example be made of $Fe_3O_4$. Different types of suitable particles and coatings are listed in WO99/49319. An example of suitable magnetic microbeads are Streptavidine MagneSphere® Paramagnetic Particles available from Promega Corporation, Madison, USA. Such particles have a 1 µm diameter, and $\chi_{eff}$ approximately 0.8.

The coil array 20 for example has the layout shown in FIG. 3 and FIGS. 8-12. It comprises a series of overlapping coils 22 produced using standard Printed Circuit Board (PCB) technology. The coils 22 are for instance made of copper, 100 µm winding width, 35 µm winding height, 200 µm winding pitch and can have a small number of windings (typically, N=4-10). A single coil 22 of the given dimensions typically generates a magnetic field gradient of about 5 mT/mm for a maximum allowed current density of 400 A/mm$^2$.

One should note that the coil 22 at its centre has no windings, indicating the need of having a feed through to another functional layer of the Printed Circuit Board. However, in practice, one will fill the coil 22 as much as possible with electrical windings.

Figure 2:
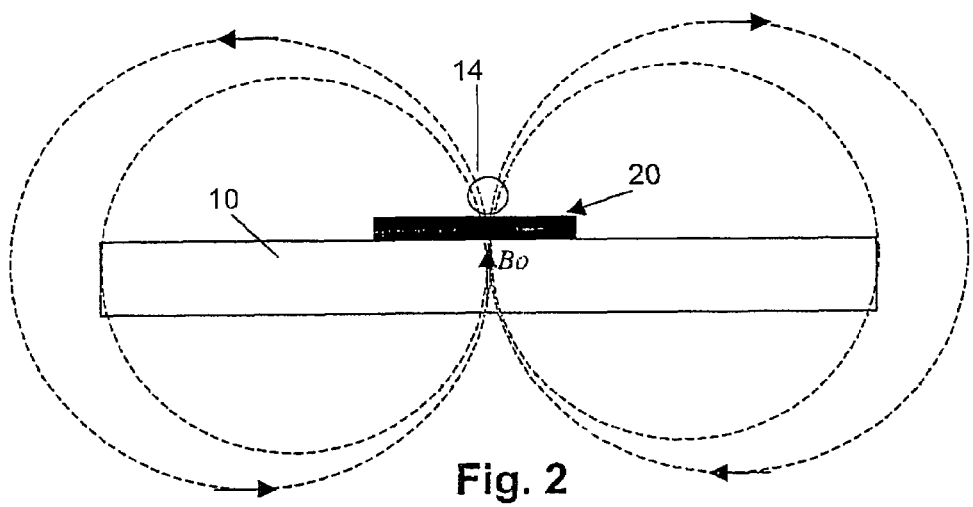
FIG. 2 is a lateral view of a second embodiment of a bead transport device according to the invention employing a single permanent magnet.
Figure 3:
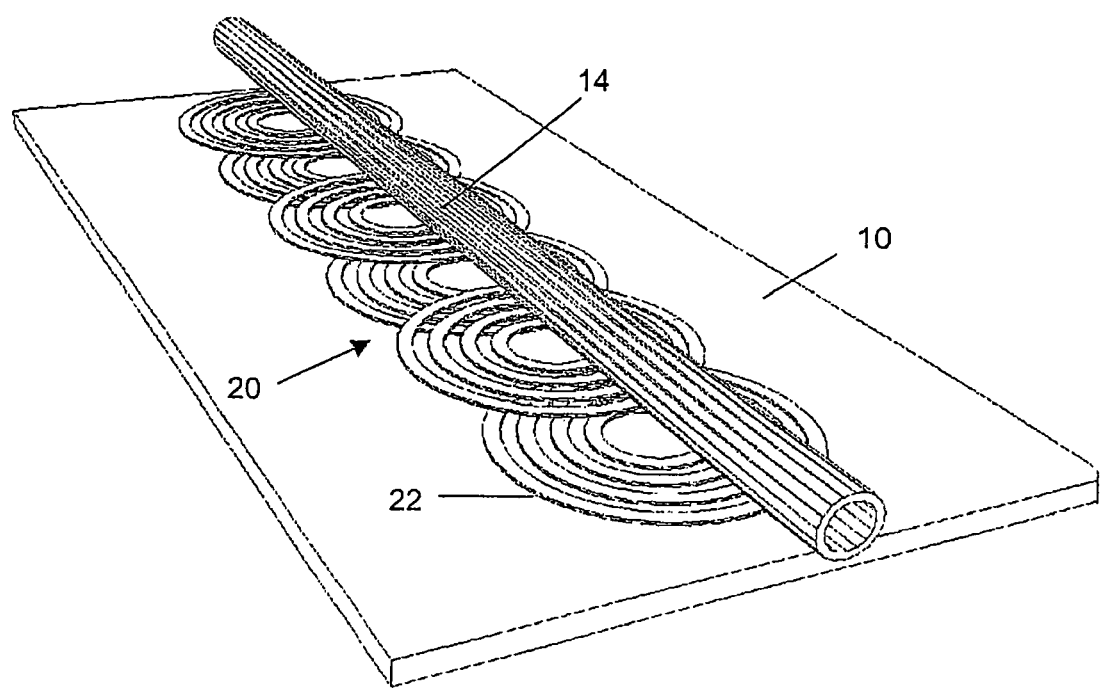
FIG. 3 is a perspective view of the centre part of the device of FIG. 2.

FIGS. 2 and 3 show a second example of a bead transport structure according to the invention in schematic lateral view and in perspective, respectively. In this example the coil array 20 and capillary 14 are placed centrally on a single permanent magnet 10 generating at its centre the uniform magnetic field $B_0$ (for instance 50 mT) over the total length of capillary 14.

For illustrative purposes, FIG. 3 shows the overlapping coils 22 on a support 10. In practice, however, the overlapping coils are arranged over two (or more) functional layers separated by an insulating layer or support 10.

Figure 4:
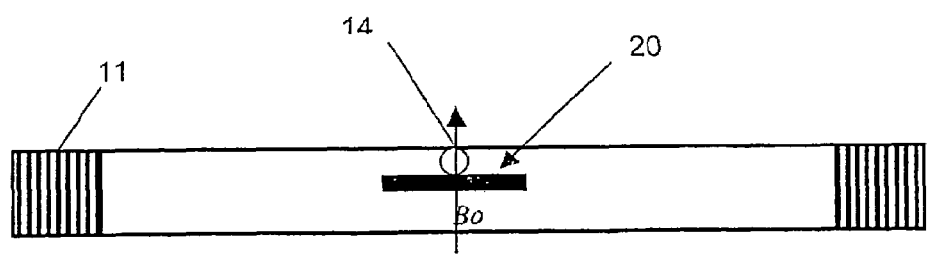
FIG. 4 is a lateral view of a third embodiment of a bead transport device according to the invention employing an electromagnet generating a large static magnetic field.

FIG. 4 shows a third example of a bead transport structure according to the invention in schematic lateral view, wherein the coil array 20 and capillary 14 are placed centrally in an electromagnet 11 generating along its central axis the uniform magnetic field $B_0$ (for instance 50 mT) over the total length of capillary 14.

A special feature of the inventive device is the partial overlap of adjacent coils 22 (as shown in FIG. 3 and FIGS. 8-12), so that there is never a local magnetic energy minimum in between two coils 22. This is to be contrasted with the simple juxtaposition of the prior art that cannot provide microbead transport, but merely allows separation of microbeads transported by a moving fluid.

FIGS. 6 and 7 respectively show how the field produced by a coil 22 can be used to attract or to repel microbeads 25. As shown in FIG. 6, when the field produced by coil 22 is parallel to the uniform field $B_0$, the microbeads 25 above the coil 22 are attracted towards the open centre of the coil 22 formed by its inner turn 23. The distribution of this magnetic field produced by the coil 22 is illustrated in FIG. 5. As shown in FIG. 7, when the field produced by coil 22 is antiparallel to the uniform field $B_0$, the microbeads 25 above the coil 25 are repelled towards the exterior part of the coil 22 formed by its outer turn 24.

By switching the direction of the current in the coil 2, microbeads 25 in a fluid in a capillary chamber above the coil 22 can be made to move between the equilibrium positions at the periphery and the centre of the coil 22.

The current actuation scheme of these coils 22 constitutes another innovative aspect. One should note that, due to finite size of the cluster, not all microbeads will be subjected to the same force. Therefore care needs to be taken to transport effectively all microbeads in a given direction. Consider a system consisting of at least three neighbouring coils 22, as for example illustrated in FIGS. 8 and 9: a first one repulsive, a middle one repulsive/attractive and a third one attractive. When the middle coil is switched from the attractive (FIG. 6) to the repulsive (FIG. 7) mode, part of the beads will go to the left and part to the right of the coil center. When thereafter, the center coil is again in the attractive mode (FIG. 6), the microbeads 25, which first have moved to the left, are now displaced to the right. By repeating the attractive and repulsive sequences, thereby creating an 'oscillatory' field, one can effectively transport all microbeads of the cluster from the left to the right.

Figure 8:
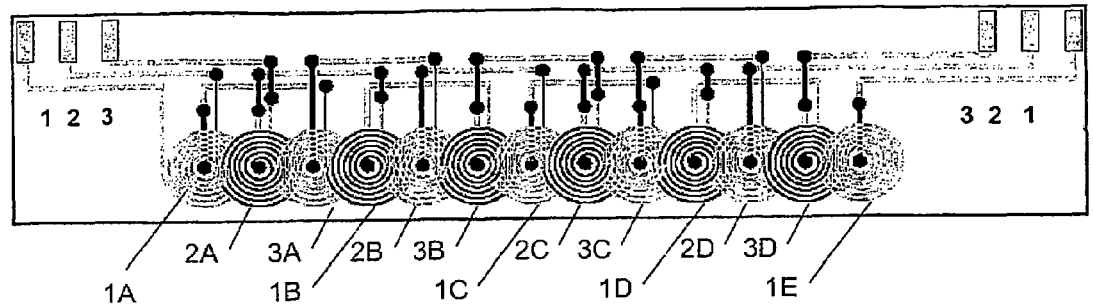
FIG. 8 is a diagram illustrating a three-phase connection of a series of overlapping coils.

FIG. 8 illustrates an arrangement wherein the coils 22 are connected in at least two series such that the magnetic field of adjacent and overlapping coils 22 can be varied independently of one another to provide a coordinated driving force on the microbeads 25, namely in this example by using a three-phase supply.

As shown in FIG. 8 series 20 of thirteen coils (numbered 1A to 1E) is realised by PCB technology on an insulating support 30 with two sets of integrated current supply terminals 1,2,3 for a three-phase supply. Starting from the left of FIG. 8, terminal 1 is connected to the outer winding of coil 1A whose inner winding is connected to the outer winding of coil 1B whose inner winding is connected in turn to the outer winding of coil 1C. The latter's inner winding is then connected in series to the outer winding of coil 1D and so on to the end coil 1E whose inner winding is connected to the corresponding terminal 1. In like manner, coil 2A is connected via coils 2B, 2C and 2D between the terminals 2, and coil 3A is connected via coils 3B, 3C and 3D between the terminals 3.

Figure 9:
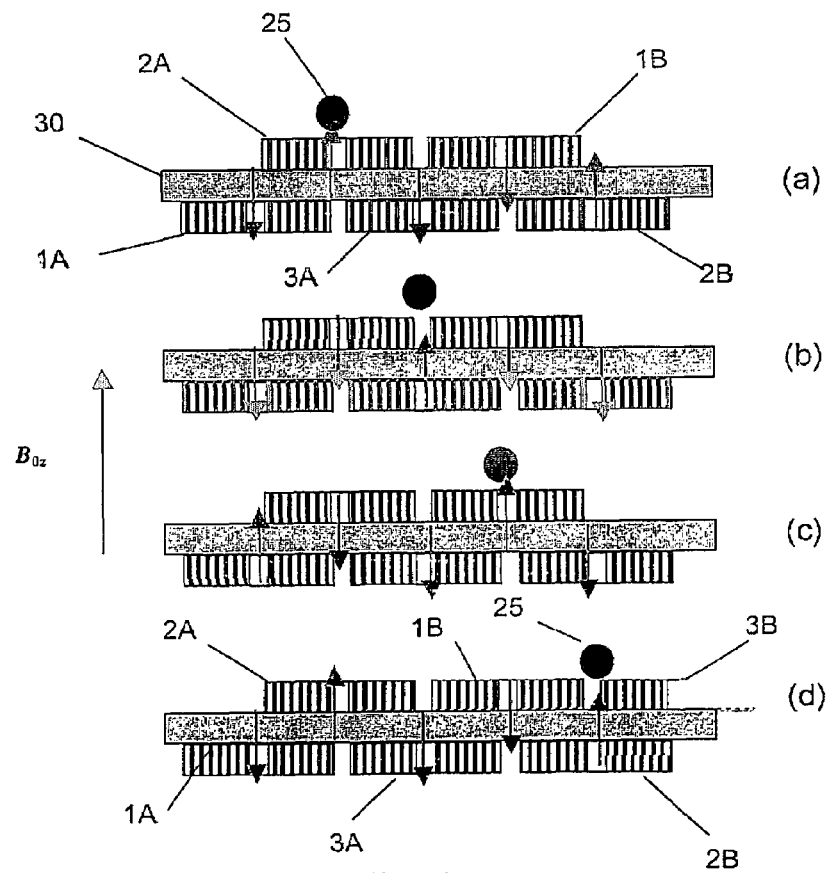
FIG. 9 is a diagram illustrating the displacement of a bead by the successive switching of a series of overlapping coils.

FIG. 9 shows how, using for example FIG. 8's 3-phase arrangement, one can combine the magnetic fields from adjacent coils 22 properly in time and create a magnetic field maximum, which propels the microbeads 25 in the capillary 14. Here we can benefit from the advantage that the permanent magnetic field imposes the magnetic moment always in the same direction of the microbeads, so that we can apply the coil-generated magnetic field ($B_z$) from up (parallel to the uniform field component $B_0$) to down (antiparallel to the uniform field component $B_0$), allowing to generate both attractive and repulsive magnetic forces. This enables the combined use and actuation of neighbouring coils 22 to generate the time- and position-dependent magnetic forces.

In FIG. 9, a succession of coils numbered 1A to 2C, as in FIG. 8, are illustrated as being located on opposite s;des of an insulating support 30. Other arrangements are of course possible, in which the coils 22 are distributed over at least two functional layers, separated by an insulating layer. In FIG. 9(a) a microbead 25 is shown at one end of the array, over the centre of coil 2A which is illustrated in the attractive mode, i.e. its field directed upwards as indicated by the arrow, parallel to the uniform field Boz. In FIG. 9(b), the current in the coils has been reversed, so the coil 2A is in repulsive mode, whereas the adjacent overlapping coil 3A is in the attractive mode. The microbead 25 is hence attracted to the centre of coil 3A, so it is displaced to the new position shown in FIG. 8(b). When the current in the coils is reversed again as shown in FIG. 8(c), the coil 3A is now repulsive and coil 1B is attractive, so the microbead 25 is displaced to the new position shown in FIG. 8(c), over the centre of coil 1B. Likewise for FIG. 9(c), where only the left hand part of coil 3B is visible. In this Figure, a further reversal of the current in the coils has brought the microbead 25 over the centre of coil 2B, in the attractive mode and between the peripheries of coils 1B and 3B, in the repulsive mode.

Arranging adjacent coils 22 with spatial overlap and actuating them in a specific three-phase sequence, as described above, allows transporting single microbeads (specifically the MagneSphere® Paramagnetic Particles) with characteristic velocities of 0.1 mm/s, and complete clusters of beads with an effective velocity of the order of several 0.1 mm/s. For these beads in water, it was found that the switching time necessary for a microbead to go from the centre to the border of a coil was about 0.2 sec, corresponding to a maximum switching frequency of 5 Hz.

Figure 10:
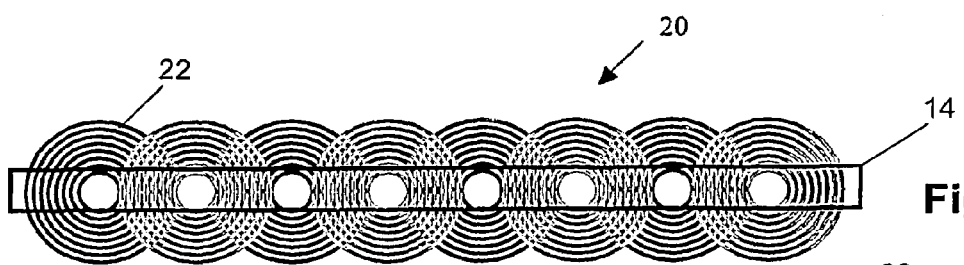
FIG. 10 is a diagrammatic plan view of a series of overlapping coils with a single capillary tube.
Figure 11:
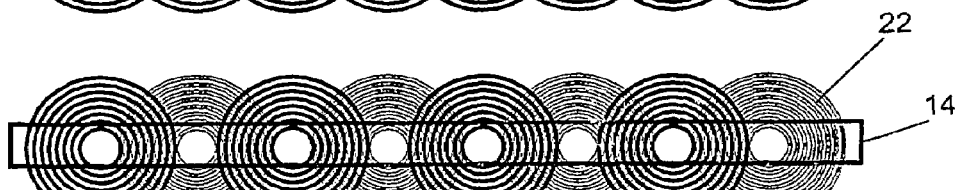
FIG. 11 is a similar view showing an array of side-by-side series of overlapping coils with respective capillary tubes.
Figure 12:
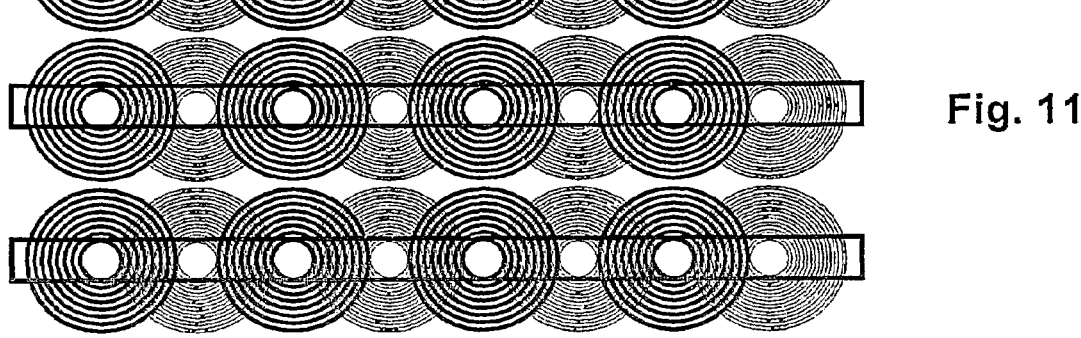
FIG. 12 is a similar view showing another array of overlapping coils with a single capillary chamber extending over the array.

FIGS. 10, 11 and 12 schematically show several arrangements for transporting microbeads in one direction (FIGS. 10 and 11) or in several directions in a two-dimensional arrangement (FIG. 12).

FIG. 10 illustrates a row 20 of coils 22 associated with a rectilinear capillary channel 14 extending along the row, over the centres of the overlapping coils, enabling transport of microbeads along the capillary channel 14, as explained with reference to FIGS. 8 and 9.

FIG. 11 illustrates an arrangement that consists of a juxtaposition of several rows as illustrated in FIG. 10, side-by-side. In this arrangement, each row of coils 22 is associated with its own capillary channel 14.

FIG. 12 illustrates an array of overlapping coils 22 arranged along alternate rows, in quincunx in the illustrated example. In this case, a capillary chamber 14 extends over the open centres of the array of coils 22, i.e over several rows of coils. As indicated at 40, the centres of the coils in this arrangement form a hexagon. The walls of the chamber 14 can, but do not need to, be grooved or channeled in correspondence with the hexagons 40 to guide the microbeads. When the currents in the overlapping coils are reversed, microbeads can be displaced in the capillary chamber 14 along the lines of this hexagon 40, from the centre of one coil 22 to the next. If desired, with this arrangement, individual coils 22 can be selectively addressed so that by selective actuation of the coils the microbeads 25 can be guided along given paths to facilitate their separation.

Hence, two-dimensional magnetic circuits are possible by placing a two-dimensional coil array 20 over a large surface area where there is a constant field generated by permanent magnets. The microbeads will not have a preferential position if the magnetic induction is constant, but the actuation of a two-dimensional array of coils will allow transport in two dimensions inside a microfluidic structure. Or beads can be transported in a complex microfluidic system, containing numerous channels, reactors, etc.

In one application, a bottom surface of the capillary chamber 14 is bio-chemically activated for the retention of molecules or substances to be detected, and the microbeads 25 are coated with a biological active layer selectively retainable by said molecules or substances such that when the microbeads are transported in the capillary chamber 14 by the coil(s) 22 the transported microbeads 25 can be retained by the molecules or substances to be detected and thus be separated from the transported microbeads.

In another application, the capillary chamber 14 is part of a microfluid circuit comprising a Hall sensor, the coil(s) 22 being arranged to transport the microbeads to the Hall sensor which recognises the presence of a microbead, specifically bound on top of it.

Many modifications of the described embodiments of the device are possible and the device can be used for many applications, other than those described, e.g. magnetic filtration.

The invention claimed is:

1. A device for transporting magnetic or magnetisable microbeads in a capillary chamber, comprising:
    a capillary chamber containing magnetic or magnetisable microbeads in a fluid;
    means for subjecting the capillary chamber to a substantially uniform magnetic field, to induce a permanent magnetic moment to the microbeads;
    an array of a plurality of coils adjacent to the capillary chamber, each coil for applying a complementary magnetic field on the microbeads parallel or antiparallel to said substantially uniform magnetic field, the coils in said array being arranged in overlapping relationship to avoid a local energy minimum between any two coils, with the center of each coil in the proximity of an edge of an adjacent coil; and
    means for switching the current applied to the coils to invert the field produced thereby, to selectively apply a driving force on the microbeads in the capillary chamber;
    the capillary chamber extending over the centers of the plurality of coils in the array to permit, in response to the application of said driving force by said switching means to successive coils, driving of the microbeads in the capillary chamber from center to center of adjacent coils and then to the next adjacent coils in the array whereby the microbeads can be driven over the array of coils.

2. The device of claim 1, wherein the substantially uniform magnetic field is generated by at least one permanent magnet.

3. The device of claim 2, wherein the substantially uniform magnetic field is generated by two permanent magnets spaced apart from one another on top of a soft magnetic sheet on which is placed the array of coils and the capillary chamber.

4. The device of claim 2, wherein the substantially uniform magnetic field is generated by a single permanent magnet on which is placed the array of coils and the capillary chamber.

5. The device of claim 2, wherein the substantially uniform magnetic field is generated along an axis of an electromagnet, the array of coils and the capillary chamber being placed in the axis of the electromagnet.

6. The device of claim 1 comprising overlapping substantially circular, oval, square, polygonal, rectangular or triangular coils of like dimensions, the outer winding of each coil overlapping with the inner winding of an adjacent coil.

7. The device of claim 6, comprising an array of overlapping coils arranged along alternate rows, and a capillary chamber which extends over the centers of the array of coils.

8. The device of claim 7, wherein the switching means is arranged to displace microbeads along paths extending through the array between the centres of adjacent overlapping coils.

9. The device of claim 1, comprising at least one row of overlapping coils aligned along a substantially rectilinear axis, and at least one capillary chamber which extends along said substantially rectilinear axis over the centers of the coils.

10. The device of claim 9, wherein the switching means is arranged to displace microbeads along a substantially rectilinear path along the capillary chamber(s).

11. The device of claim 1, wherein coils are connected in at least two series such that the magnetic field of adjacent and overlapping coils can be varied independently of one another.

12. The device of claim 1, wherein the uniform magnetic field is in the range $10^4$-$10^8$ A/m$^2$ and the field generated by the overlapping coils has a gradient in the range $10^4$-$10^8$ A/m$^2$.

13. The device according to claim 1 wherein the microbeads have dimensions from 0.01 to 10 μm.

14. The device according to claim 1 wherein the coils are PCB coils producible by PCB technology.

15. The device according to claim 1, wherein the coils are generally planar and said substantially uniform magnetic field is perpendicular to the planar coils.

16. The device according to claim 1 comprising overlapping coils arranged over at least two functional layers separated by an insulating layer.

17. The device according to claim 1, wherein a bottom surface of the capillary chamber is bio-chemically activated for the retention of molecules or substances to be detected, and the microbeads are coated with a biological active layer selectively retainable by said molecules or substances such that when the microbeads are transported in the capillary chamber by the coils the transported microbeads can be retained by the molecules or substances to be detected and thus be separated from the transported microbeads.

18. The device according to claim 1, wherein the capillary chamber is part of a microfluid circuit comprising a Hall sensor, the coils being arranged to transport the microbeads to the Hall sensor.

19. A bio-analysis system incorporating at least one device according to claim 1.

20. A diagnostic system incorporating at least one device according to claim 1.

21. A method of transporting microbeads in a fluid in a capillary chamber, which comprises:
    subjecting the capillary chamber to a substantially uniform magnetic field, to induce a permanent magnetic moment to the microbeads;
    applying a complementary magnetic field on the microbeads parallel or antiparallel to said substantially uniform magnetic field by means of an array of a plurality of coils adjacent to the capillary chamber, each coil for applying the complementary magnetic field on the microbeads parallel or antiparallel to said substantially uniform magnetic field, the coils in said array being arranged in overlapping relationship to avoid a local energy minimum between any two coils, with the center of each coil in the proximity of an edge of an adjacent coil; and
    switching the current applied to the coils to invert the field produced thereby, to selectively apply an attractive or repulsive driving force on the microbeads;
    the capillary chamber extending over the centers of the plurality of coils in the array whereby, in response to the application of said driving force by said switching means to successive coils, the microbeads in the capillary chamber are driven from center to center of adjacent coils and then to the next adjacent coils in the array so the microbeads can be driven over the array of coils.

22. The method of claim 21 wherein the coils are generally planar and said substantially uniform magnetic field is perpindicular to the planar coils.

23. A method of using the device according to claim 1 for carrying out a chemical or biochemical reaction or assay or a diagnostic method.

24. A method of using the device according to claim 23, wherein the microbeads have a biologically active surface for detecting molecules or substances retained on a biochemically activated bottom surface of the capillary.

* * * * *